United States Patent
Lazic

(10) Patent No.: US 10,226,252 B2
(45) Date of Patent: Mar. 12, 2019

(54) SURGICAL CLIP WITH THREE CLAMPING ARMS

(71) Applicant: Peter Lazic GmbH, Tuttlingen (DE)

(72) Inventor: Daniel Lazic, Tuttlingen (DE)

(73) Assignee: PETER LAZIC GMBH, Tuttlingen (DE)

( * ) Notice: Subject to any disclaimer, the term of this patent is extended or adjusted under 35 U.S.C. 154(b) by 240 days.

(21) Appl. No.: 14/670,709

(22) Filed: Mar. 27, 2015

(65) Prior Publication Data

US 2015/0289876 A1    Oct. 15, 2015

(30) Foreign Application Priority Data

Apr. 10, 2014   (EP) .................................... 14164160

(51) Int. Cl.
*A61B 17/11*     (2006.01)
*A61B 17/122*    (2006.01)
*A61B 17/00*     (2006.01)

(52) U.S. Cl.
CPC .......... *A61B 17/11* (2013.01); *A61B 17/1227* (2013.01); *A61B 2017/00473* (2013.01); *A61B 2017/1103* (2013.01); *A61B 2017/1107* (2013.01); *A61B 2017/1132* (2013.01); *A61B 2017/1139* (2013.01)

(58) Field of Classification Search
CPC ....... A61B 17/08; A61B 17/083; A61B 17/11; A61B 17/12; A61B 17/122; A61B 17/1227; A61B 2017/1107; A61B 2017/1121; A61B 2017/1132; A61B 2017/12004; Y10T 24/44325

See application file for complete search history.

(56) References Cited

U.S. PATENT DOCUMENTS

| | | | | |
|---|---|---|---|---|
| 2,416,733 | A | * | 3/1947 | Berndt ....................... B66C 1/12 24/132 R |
| 6,517,554 | B1 | * | 2/2003 | Zhu ......................... A61B 17/30 606/150 |
| 8,273,096 | B2 | * | 9/2012 | Lazic ................. A61B 17/1227 24/510 |
| 2002/0111643 | A1 | * | 8/2002 | Herrmann .......... A61B 17/1227 606/158 |
| 2014/0364882 | A1 | * | 12/2014 | Tulleken ................ A61B 17/11 606/153 |

FOREIGN PATENT DOCUMENTS

| | | |
|---|---|---|
| DE | 203 03 496 U1 | 7/2003 |
| DE | 10 2004 016 859 A1 | 10/2005 |
| DE | 10 2009 003273 A1 | 11/2010 |

* cited by examiner

*Primary Examiner* — Todd Scherbel
(74) *Attorney, Agent, or Firm* — Hackler Daghighian Martino & Novak

(57) ABSTRACT

A surgical clip includes three double-armed clip parts that are mounted to be rotatable about an axis of rotation and each comprise one operating arm and one clamping arm, wherein a middle clip part is arranged such that its operating arm is arranged between the operating arms of the two outer clip parts and its clamping arm is arranged between the clamping arms of the two outer clip parts, as well as a spring that pretensions the two outer clip parts into a closed clip position in which the clamping arms of the three clip parts abut one another.

12 Claims, 5 Drawing Sheets

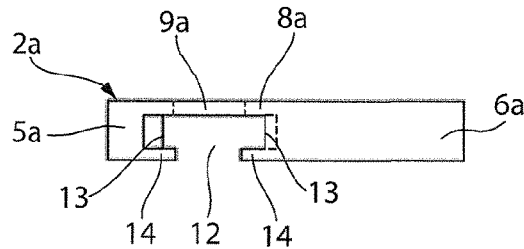
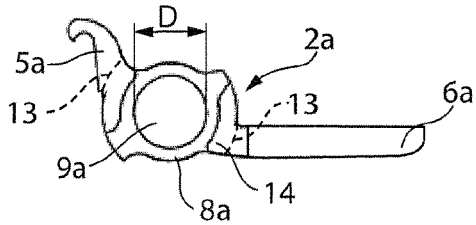
Fig. 2a  Fig. 2b
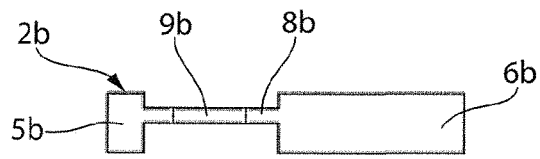
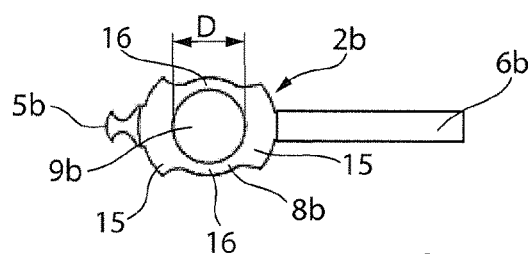
Fig. 3a  Fig. 3b
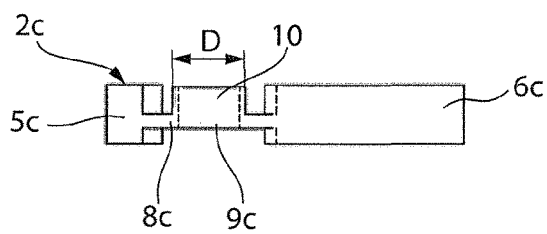
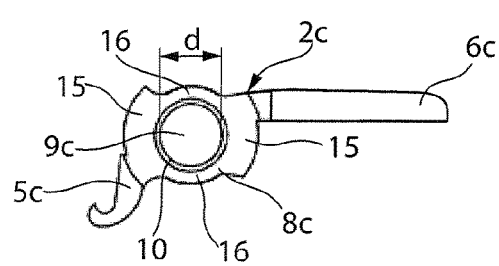
Fig. 4a  Fig. 4b
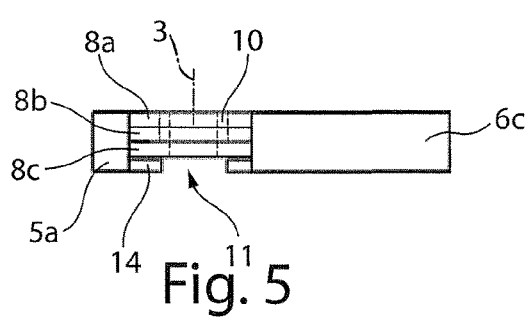
Fig. 5

SURGICAL CLIP WITH THREE CLAMPING ARMS

CROSS-REFERENCE TO RELATED APPLICATIONS

This application claims priority to European Patent Application No. 14 164 160.5, filed Apr. 10, 2014, the entire contents of which are hereby incorporated by reference.

DESCRIPTION

Field of the Invention

The invention relates to a surgical clip with clamping arms, which is used for clamping hollow organs, in particular blood vessels, or for connecting two blood vessels.

BACKGROUND OF THE INVENTION

DE 10 2004 016 859 A1 and DE 10 2009 003 273 A1 disclose aneurysm clips with two rotatably mounted clip parts, each of which comprises one operating arm and one clamping arm. A helical or leg spring is arranged in a central opening of the two clip parts, the spring legs of which are welded to the two clip parts in order to pretension the two clip parts into a closed clip position in which the two clamping arms abut one another.

It is the object of the present invention to provide a surgical clip that can be used in a variety of ways and can, in particular, also be used to connect two vessels.

SUMMARY OF THE INVENTION

This object is achieved in accordance with the invention with a surgical clip comprising three double-armed clip parts that are mounted to be rotatable about an axis of rotation and each comprise one operating arm and one clamping arm, wherein the middle clip part is arranged such that its operating arm is arranged between the operating arms of the two outer clip parts and its clamping arm is arranged between the clamping arms of the two outer clip parts, and comprising a spring that pretensions the two outer clip parts into a closed clip position in which the clamping arms of the three clip parts abut one another.

In accordance with the invention, the spring only engages on the two outer clip parts such that the middle clip element is mounted between the two outer clip parts such that it can freely rotate. The middle clamping arm and electively one of the two outer clamping arms can be opened with respect to each other by means of an applying forceps that spreads open the middle operating arm and one of the two outer operating arms, wherein the middle clamping arm carries along the other outer clamping arm, which abuts the outside, in an outward direction, namely against the closing force of the spring that acts between the two outer clip parts. While the middle clamping arm and one of the outer clamping arms are opened, the other outer clamping arm is held in abutment on the middle clamping arm, i.e. the middle clamping arm and the other outer clamping arm remain in the closed position. For this reason, a first vessel can be clamped between the middle clamping arm and one of the outer clamping arms and a second vessel can subsequently be clamped between the middle clamping arm and the other outer clamping arm without having to release clamping of the first vessel. As a result, two vessels are simultaneously clamped to the clip.

In one preferred embodiment of the invention, one of the three clip parts has a bearing shaft or bearing sleeve between its clamping and operating arms, which is formed thereon in one piece or is fixed such that it cannot rotate relative to the clip part, whereas the other two clip parts each have a bearing opening between their clamping and operating arms, by means of which they are mounted on the bearing shaft/bearing sleeve such that they can rotate about the axis of rotation. The bearing shaft/bearing sleeve thus forms the pivot bearing about which the other two clip parts rotate. In this embodiment, the inventive clip thus consists of four individual parts, i.e. the three clip parts and the spring.

In another preferred embodiment of the invention, each of the three clip parts comprises a bearing opening between its clamping and operating arms, by means of which bearing openings, the clip parts are mounted on a separate bearing shaft or bearing sleeve such that they can rotate about the axis of rotation. The bearing shaft/bearing sleeve is put through the bearing openings of the three clip parts and thus forms the pivot bearing about which the three clip parts rotate. In this embodiment, the inventive clip thus consists of five individual parts, i.e. the three clip parts, the bearing shaft/bearing sleeve and the spring. The spring can alternatively also serve as pivot bearing instead of a separate bearing shaft/bearing sleeve, wherein the bearing openings of the three clip parts rotate on the spring. In this embodiment, the clip thus consists of four individual parts, i.e. the three clip parts and the spring.

The two spring ends of the spring are preferably connected to the two outer clip parts in a material-bonding manner, in particular through welding. The spring legs can alternatively only be clamped around the outer side of the outer clip parts—similar to the leg spring of a clothespin.

The spring is preferentially designed as a leg spring, the two spring legs of which engage on the two outer clip parts. In case of a bearing sleeve, all coil turns, i.e. the overall spring winding body of the leg spring, are completely arranged within the bearing sleeve, if possible, in order to prevent bruises of tissue between the individual coil turns of the leg spring.

In case of a welded-on spring, the compound of the three rotatably mounted clip parts can, in principle, be held together by the welded-on spring. Additionally, or in case the spring is not welded-on, one of the three clip parts preferably has a receiving area between its clamping and operating arms, into which the other two clip parts are axially inserted in an assembly rotary position and are axially interlocked by subsequent rotation in a direction towards the closed clip position. This plug-rotation lock enables nesting and rotary guidance of the clip parts without additional components and without additional assembly effort. In case of a separate bearing sleeve, the bearing sleeve has an annular collar at one end and a rivet head bent to the outside at the other end such that the three clip parts are axially held together between the annular collar and the rivet head.

The clamping arms are either designed in one piece with their clamping arm ends or each clamping arm is designed in two pieces with a clamping arm base and a clamping arm end, wherein the clamping arm base has an interface for fastening the clamping arm end.

In one particularly preferred embodiment of the inventive clip, each clamping arm end is designed as a ring, wherein the rings abut each other in the closed clip position and the ring openings, which are in particular of identical size, form a through-hole. This clip is particularly suited for bypass operations, in which two blood vessels are connected to each other. The two vessels must normally be sewed together which requires a large amount of time and great precision of the operating surgeon. The two open vessel ends are each turned inside out over the rings of the outer clip parts and clamped by the ring of the middle clip part, thereby connecting the two vessel ends to each other without sewing.

In another preferred embodiment of the inventive clip, the clamping arms of the two outer clip parts are each designed as a fork and the clamping arm of the middle clip part is designed as a ring, which enables connection of two vessel walls to each other.

In a further preferred embodiment of the inventive clip, the clamping arm of one of the two outer clip parts is designed as a fork and the clamping arms of the other two clip parts are each designed as a ring, which enables connection of one vessel end to one vessel wall.

The invention also relates to a method for connecting two vessels, in particular two blood vessels, by means of the above-described surgical clips, comprising the steps of the first method claim.

The invention also relates to a method for connecting the open vessel ends of two vessels by means of the above-described surgical clip, comprising the steps of the second method claim.

The invention also relates to a method for connecting a vessel wall and a vessel end by means of the above-described surgical clip, comprising the steps of the third method claim.

These techniques considerably facilitate connection of two vessels, in particular, in bypass operations. After fixing of the first vessel, the second vessel can subsequently be fixed without thereby having to release the connection of the first vessel. The two open vessel ends are each clamped by the ring of the middle clip part after turning them inside out over the rings of the outer clip parts, thereby connecting the two vessel ends to each other without sewing.

Further advantages of the invention can be extracted from the description, the claims and the drawing. The features mentioned above and below may be used individually or collectively in arbitrary combination. The embodiments illustrated and described are not to be understood as exhaustive enumeration but have exemplary character for describing the invention.

BRIEF DESCRIPTION OF THE DRAWINGS

The accompanying drawings illustrate the invention. In such drawings:

FIGS. 2a, 2b show the one outer clip part of the clip shown in FIG. 1 in side view (FIG. 2a) and in axial top view (FIG. 2b);

FIGS. 3a, 3b show the middle clip part of the clip shown in FIG. 1 in side view (FIG. 3a) and in axial top view (FIG. 3b);

FIGS. 4a, 4b show the other outer clip part of the clip shown in FIG. 1 in side view (FIG. 4a) and in axial top view (FIG. 4b);

FIG. 5 shows the three clip parts shown in FIGS. 2 to 4, which are connected to each other by means of a plug-rotation lock;

DETAILED DESCRIPTION OF THE PREFERRED EMBODIMENTS

Figure 1A:
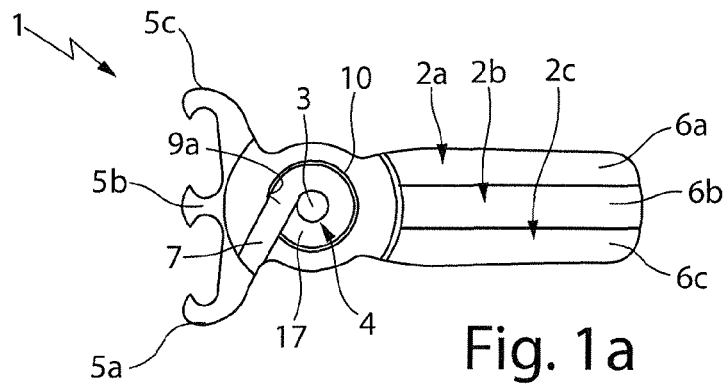
FIGS. 1a-1c show an inventive surgical clip comprising three rotatably mounted double-armed clip parts in a closed clip position (FIG. 1a), in a first open clip position (FIG. 1b), and in a second open clip position (FIG. 1c)

In the following description of the drawing, identical components or components having identical functions are designated by the same reference numerals.

The surgical clip 1 shown in FIG. 1a comprises three double-armed clip parts 2a, 2b, 2c, which are connected to each other such that they can be rotated about an axis of rotation 3 and are pretensioned by a leg spring 4 into their closed clip position shown in FIG. 1a.

The double-armed clip parts 2a, 2b, 2c each have a short operating arm 5a, 5b, 5c and a long clamping arm 6a, 6b, 6c. The operating arm 5b of the middle clip part 2b is arranged between the operating arms 5a, 5c of the two outer clip parts 2a, 2c, and its clamping arm 6b is arranged between the clamping arms 6a, 6c of the two outer clip parts 2a, 2c. The operating and clamping arms 5a, 6a and respectively 5c, 6c of each outer clip part 2a, 2c are disposed opposite to each other with respect to the axis of rotation 3 and are offset parallel to each other such that the two outer clip parts 2a, 2c intersect with respect to the axis of rotation 3. The two spring legs 7 of the leg spring 4 are welded to the two outer clamping arms 6a, 6c, the leg spring 4 thereby pretensioning the two outer clip parts 2a, 2c into the closed clip position, in which the clamping arms 6a, 6b, 6c abut each other.

The middle clamping arm 6b and the associated outer clamping arm 6a or 6c can each be opened relative to each other against the closing force of the leg spring 4 by means of an applying forceps (not shown) which grasps between the middle operating arm 5b and one of the two outer operating arms 5a or 5c and spreads them open. To be more precise, the middle clamping arm 6b carries along the abutting other outer clamping arm 6c or 6a in its opening direction during opening, i.e. against the closing force of the leg spring 4 that acts on the other outer clamping arm 6c or 6a.

Figure 1B:
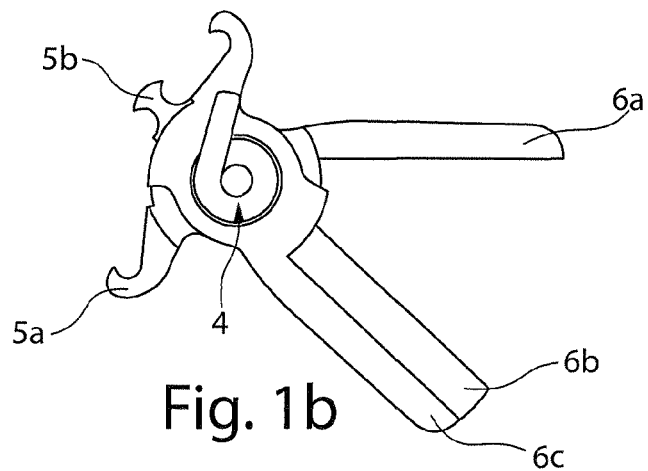
Figure 1C:
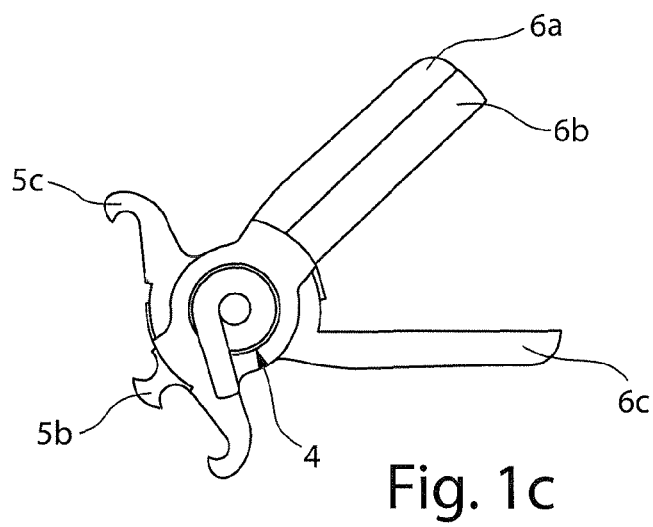

In FIG. 1b, the middle operating arm 5b and the lower outer operating arm 5a are spread open and for this reason, the middle clamping arm 6b and the upper outer clamping arm 6a are open with respect to each other. The lower outer clamping arm 6c that abuts the middle clamping arm 6b is carried along in the opening direction by the middle clamping arm 6b against the closing force of the leg spring 4. In FIG. 1c, the middle operating arm 5b and the upper outer operating arms 5c are spread open, thereby opening the middle clamping arm 6b and the lower outer clamping arm 6c with respect to each other. The upper outer clamping arm 6a that abuts the middle clamping arm 6b is thereby carried along in the opening direction by the middle clamping arm 6b against the closing force of the leg spring 4.

As is shown in FIGS. 2a and 2b, one 2a of the outer clip parts has a flat annular section 8a with a circular bearing opening 9a (opening diameter D) between the operating and clamping arms 5a, 6a. As is shown in FIGS. 3a and 3b, the middle clip part 2b also has a flat annular section 8b with a circular bearing opening 9b (opening diameter D) between the operating and clamping arms 5b, 6b. As is shown in FIGS. 4a and 4b, the other outer clip part 2c has a flat annular section 8c with a formed-on axial bearing sleeve 10 (outer diameter D, inner diameter d) between the operating and clamping arms 5c, 6c, the bearing sleeve opening being designated by reference numeral 9c.

As is shown in FIG. 5, the bearing openings 9a, 9b of the two clip parts 2a, 2b are placed onto the bearing sleeve 10 of the clip part 2c and are therefore mounted to be rotatable with respect to each other about the axis 3 of the bearing sleeve 10. The three clip parts 2a, 2b, 2c are moreover axially connected to each other by a plug-rotation lock 11. The outer clip part 2a has an axially open receiving area 12 for the annular sections 8b, 8c of the other two clip parts 2b, 2c, the bottom of which is formed by the annular section 9a. The receiving area 12 is formed by two side walls 13 that are opposite to each other with respect to the bearing opening 9a, each side wall overlapping the annular section 9a with a projection 14 at a distance that corresponds to the thickness of the two annular sections 8b, 8b. The two annular sections 8b, 8c of the other two clip parts 2b, 2c each have two first annular segments 15 disposed opposite to each other with respect to the bearing or sleeve opening 9b, 9c, and between each of these a second annular segment 16, wherein the second annular segments 16 are radially set back to the inside with respect to the first annular segments 15.

For assembling the clip 1, the second annular segments 16 of the two clip parts 2b, 2c are aligned between the two projections 14 of the clip part 2a and are axially nested into one another in this maximally open rotary assembly position, at the same time placing the clip parts 2b, 2c onto the bearing sleeve 10 of the clip part 2c. The two clip parts 2b, 2c are subsequently rotated towards the closed clip position to achieve the plug-rotation lock, thereby axially connecting the first annular segments 15 of the clip parts 2b, 2c between the annular section 8a and the projections 14 and locking them against the connection direction. The spring winding body 17 (FIG. 1a) of the leg spring 4 is finally fitted into the bearing sleeve 10 and is then welded with its two spring legs 7 to the outer side of the clamping arms 6a, 6c with pretension in order to pretension the clip parts 2a, 2c already in their closed clip position. In this embodiment, the clip 1 thus consists of four individual parts, i.e. the three clip parts 2a, 2b, 2c and the spring 4.

Figure 6:
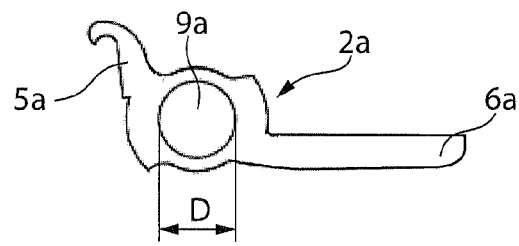
FIGS. 6, 7 and 8 each show an axial top view of a second embodiment of the three clip parts.
Figure 7:
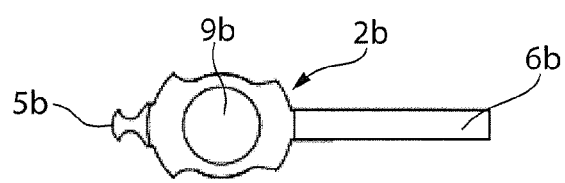
Figure 8:
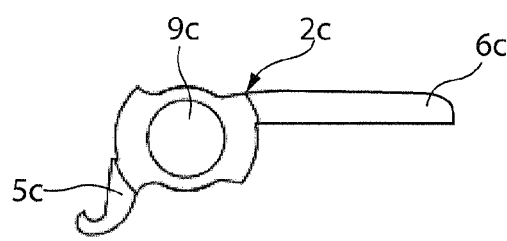
Figure 9:
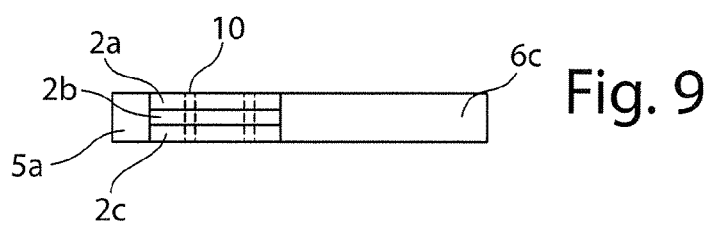
FIG. 9 shows the three clip parts shown in FIGS. 6 to 8, which are rotatably mounted on a separate bearing sleeve.

FIGS. 6 and 8 show the three clip parts 2a, 2b, 2c of a modified clip, in which the bearing sleeve 10 is not part of a clip part but a separate part and each of the three clip parts 2a, 2b, 2c has the same bearing opening 9a, 9b, 9c with diameter D. The bearing sleeve 10 is then inserted through these bearing openings 9a, 9b, 9c (FIG. 9), wherein the round outer diameter of the bearing sleeve corresponds to the opening diameter D of the circular bearing openings except for a minimum bearing play. The bearing sleeve 10 thus forms the pivot bearing about which all three clip parts rotate. The spring winding body 17 of the leg spring 4 is finally fitted into the bearing sleeve 10 and the two spring legs 7 of the leg spring are welded to the outer side of the clamping arms 6a, 6c with pretension. In this embodiment, the clip 1 thus consists of five individual parts, i.e. the three clip parts 2a, 2b, 2c, the bearing sleeve 10 and the leg spring 4.

The pivot bearing can also be formed by a solid bearing shaft instead of a bearing sleeve, however, in this case, the spring winding body 17 must be arranged on the outside of the clip 1.

In an embodiment, which is not shown, without bearing sleeve, the spring winding body 17 of the leg spring 4, the round outer diameter of which corresponds in this case to the opening diameter D of the circular bearing openings except for a minimum bearing play, is inserted through the bearing openings 9a, 9b, 9c. The leg spring 4 thus forms the pivot bearing about which all three clip parts rotate. In this embodiment, the clip 1 thus consists of four individual parts, i.e. the three clip parts 2a, 2b, 2c and the leg spring 4.

Instead of welding the spring legs 7 to the clip parts 2a, 2c, the two spring legs 7 can alternatively be clamped around the outer side of the clamping arms 6a, 6c—similar to a clothespin. In this case, the two clip parts 2a, 2b, 2c can also be formed from non-weldable material such as e.g. plastic material, in particular from polymethylmethacrylate (PMMA) or from X-ray transparent polyetheretherketone (PEEK). In case of the separate bearing sleeve 10, the sleeve ends can e.g. be radially bent to the outside in order to undetachably mount the clip parts on the bearing sleeve 10.

Figure 10:
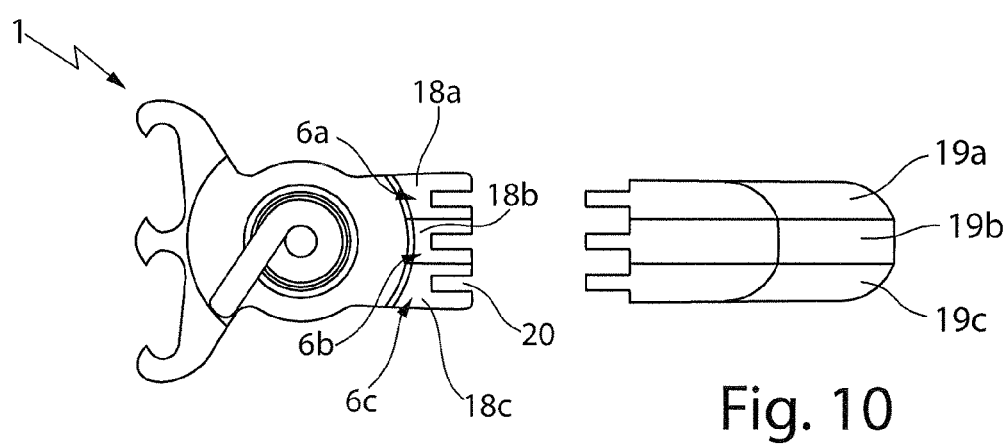
FIG. 10 shows an inventive surgical clip with clamping arms designed in two pieces.

The clip 1 shown in FIG. 10 differs from the clip 1 of FIG. 1 only in that the clamping arms 6a, 6b, 6c therein are each formed in two parts having a clamping arm base 18a, 18b, 18c and a clamping arm end 19a, 19b, 19c. The clamping arm base 18a, 18b, 18c has an interface 20 which is designed e.g. as a receiving area for optionally mounting different clamping arm ends 19a, 19b, 19c.

Figure 11:
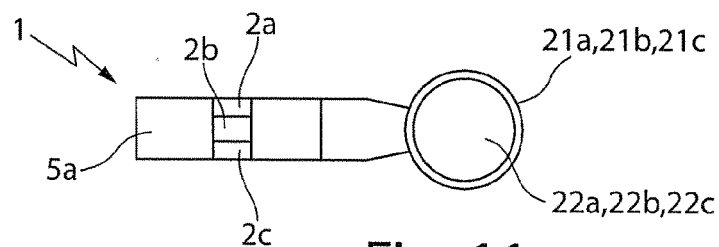
FIG. 11 shows an inventive surgical clip with annular clamping arms.

In the surgical clip 1 shown in FIG. 11, the clamping arm ends are formed in each case as rings 21a, 21b, 21c with identically sized ring openings 22a, 22b, 22c, which abut each other in the closed clip position and the ring openings 22a, 22b, 22c of which coincide to thereby form a through opening.

FIGS. 12a-12d show the individual method steps for connecting two vessels (e.g. blood vessels) 23, 24 by means of the surgical clip 1 shown in FIG. 11.

Figure 12A:
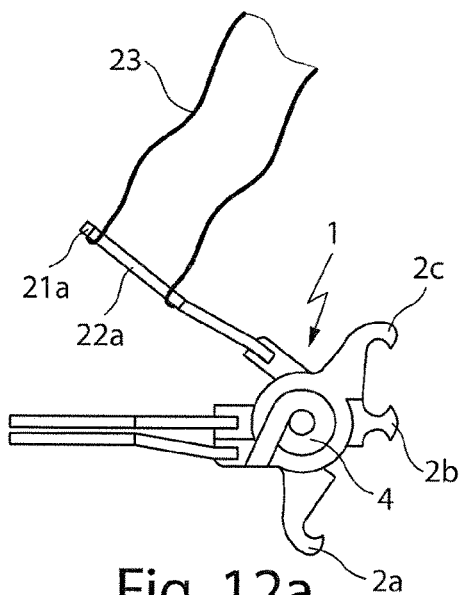
FIGS. 12a-12d show the individual method steps for connecting two vessels by means of the surgical clip shown in FIG. 11.

In FIG. 12a, the clip 1 is opened between the first outer clip part 2a and the middle clip part 2b and the open vessel end of the first blood vessel 23 is guided through the annular opening 22a of the first outer clip part 2a and then turned inside out around the ring 21a of the first outer clip part 2a.

Figure 12B:
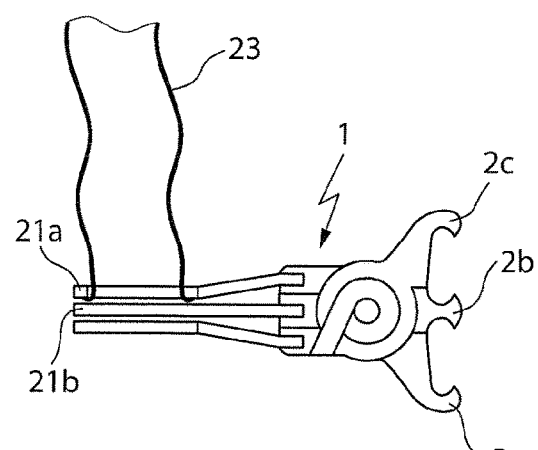

In FIG. 12b, the clip 1 is closed again, thereby clamping the vessel end, which is turned inside out, between the rings 21a, 21b of the first outer clip part 2a and of the middle clip part 2b by the closing force of the leg spring 4.

Figure 12C:
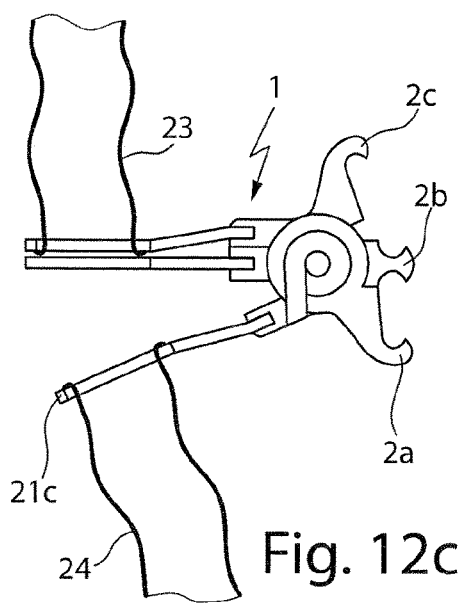

In FIG. 12c, the clip 1 is opened between the second outer clip part 2c and the middle clip part 2b and the open vessel end of the second blood vessel 24 is guided through the annular opening 22c of the second outer clip part 2c and then turned inside out around the ring 21c of the second outer clip part 2c.

Figure 12D:
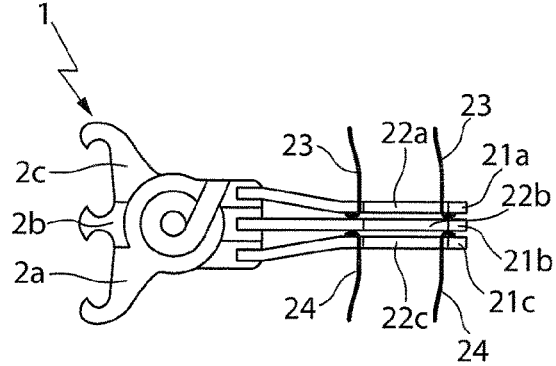

In FIG. 12d, the clip 1 is closed again, thereby clamping the vessel end, which is turned inside out, of the second blood vessel 24 between the rings 21c, 21b of the second outer clip part 2c and of the middle clip part 2b. The open vessel ends of the two blood vessels 23, 24, which have been turned inside out over the rings 21a, 21c of the outer clip parts 2a, 2c, are clamped by the ring 21b of the middle clip part 2b and connected to each other without sewing.

Figures 13A, 13B:
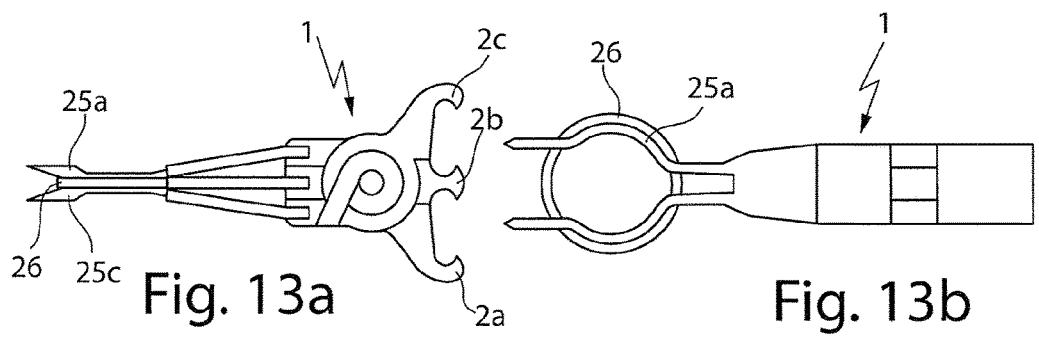
FIGS. 13a-13b show a further inventive surgical clip with an annular middle clamping arm and two double-pin-shaped outer clamping arms in side view (FIG. 13a) and in axial top view (FIG. 13b)

The clamping arm ends of the two outer clip parts 2a, 2c of the surgical clip 1 shown in FIGS. 13a, 13b, are each designed as a fork (double needle) 25a, 25c and the clamping arm end of the middle clip part 2b is designed as a ring 26. The forks 25a, 25c each have central sections that are bulged to the outside in a circular shape and abut the ring 26 of the middle clip part 2b in the closed clip position.

FIGS. 14a-14d show the individual method steps for connecting two blood vessels 23, 24 by means of the surgical clip 1 shown in FIG. 13.

Figures 14A, 14B:
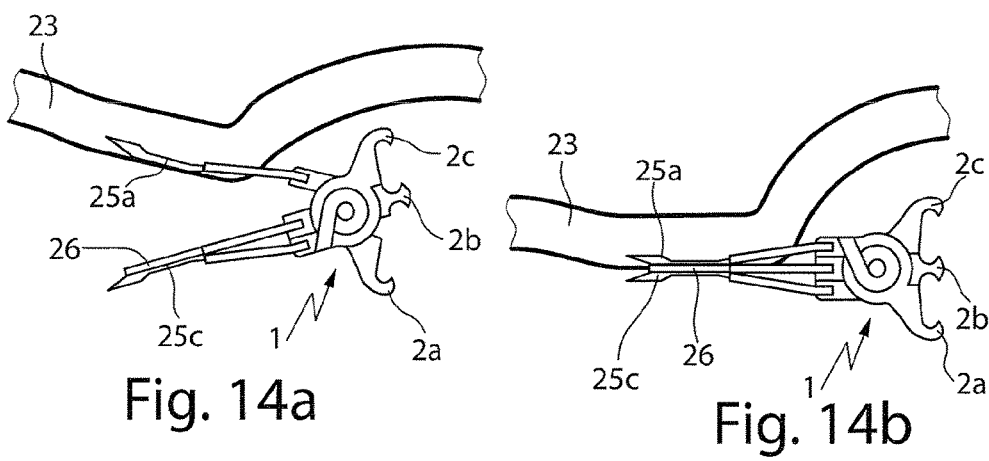
FIGS. 14a-14d show the individual method steps for connecting two vessels by means of the surgical clip shown in FIG. 13.

In FIG. 14a, the clip 1 is opened between the first outer clip part 2a and the middle clip part 2b and the fork 25a of the first outer clip part 2a is pierced into the vessel wall of the first blood vessel 23.

In FIG. 14b, the clip 1 is closed again, thereby clamping the pierced vessel wall between the fork 25a of the first outer clip part 2a and the ring 26 of the middle clip part 2b by the closing force of the leg spring 4.

Figures 14C, 14D:
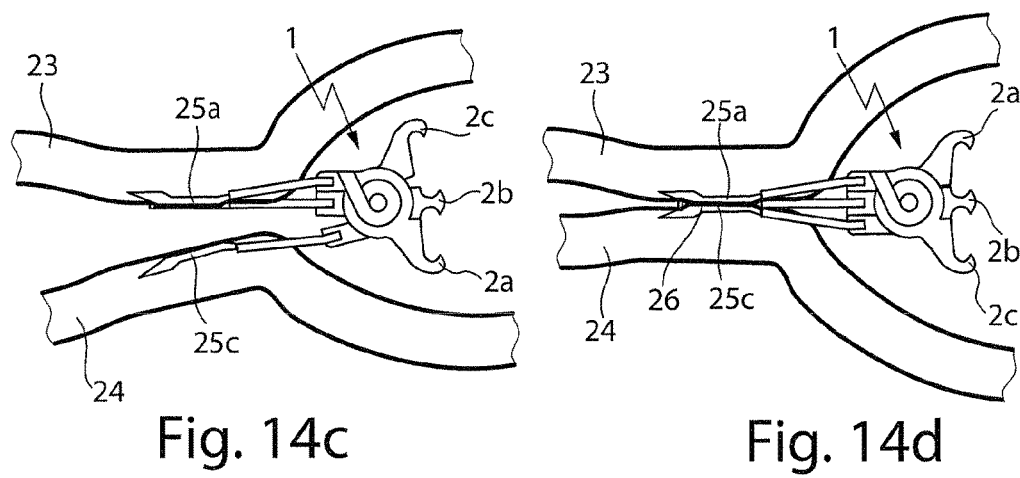

In FIG. 14c, the clip 1 is opened between the second outer clip part 2a and the middle clip part 2b and the fork 25c of the second outer clip part 2c is pierced into the vessel wall of the second blood vessel 24.

In FIG. 14d, the clip 1 is closed again, thereby clamping the pierced first blood vessel 23 between the fork 25a and the ring 26 and clamping the pierced second blood vessel 24 between the fork 25c and the ring 26. The two vessel walls are finally opened within the ring 26, thereby connecting the two blood vessels 23, 24 to each other.

In one embodiment, which is not shown, the clamping arm of one of the two outer clip parts is designed as a fork and the clamping arms of the other two clip parts are each designed as a ring in order to clamp the vessel end of a first blood vessel between the two rings and also clamp the pierced vessel wall of a second blood vessel between a ring and the fork. The pierced vessel wall is finally opened within the ring, thereby connecting the two blood vessels 23, 24 to each other.

Although several embodiments have been described in detail for purposes of illustration, various modifications may be made to each without departing from the scope and spirit of the invention. Accordingly, the invention is not to be limited, except as by the appended claims.

What is claimed is:

1. A surgical clip, comprising:
   two outer double-armed clip parts that are mounted to be rotatable about an axis of rotation and each comprise one operating arm configured to be spread open by an applying forceps and one clamping arm;
   a double-armed middle clip part that is mounted to be rotatable about the axis of rotation of the two outer double-armed clip parts, wherein the middle clip part comprises a clamping arm arranged between the clamping arms of the two outer clip parts and an operating arm arranged between the operating arms of the two outer clip parts, wherein the operating arm of the double-armed middle clip part is configured to be opened in relation to either of the operating arms of the two outer clip parts by the applying forceps engaging on a respective side of the operating arm of the middle clip part associated with the operating arm of either of the two outer clip parts in order to open the clamping arm of the middle clip part in relation to either of the clamping arms of the two outer clip parts, respectively; and
   a spring pretensioning the two outer clip parts into a closed clip position in which the clamping arms of the two outer clip parts and the middle clip part abut one another.

2. The surgical clip according to claim 1, wherein one of the two outer clip parts or the middle clip part comprises a bearing shaft or bearing sleeve between its clamping and operating arms, and the other two clip parts each comprise a bearing opening between their clamping and operating arms and are disposed on the bearing sleeve such that they can rotate about the axis of rotation.

3. The surgical clip according to claim 1, wherein each of the two outer clip parts and the middle clip part comprises a bearing opening between its clamping and operating arms, by the bearing openings the clip parts are mounted on a separate bearing shaft or bearing sleeve such that they can rotate about the axis of rotation.

4. The surgical clip according to claim 1, wherein two spring ends of the spring are connected to two outer clip parts in a material-bonding manner.

5. The surgical clip according to claim 1, wherein two spring ends of the spring are connected to two outer clip parts through welding.

6. The surgical clip according to claim 1, wherein the spring is designed as a leg spring, a winding body of which is at least partially accommodated in a bearing sleeve.

7. The surgical clip according to claim 1, wherein one of two outer clip parts or the middle clip part comprises a receiving area between its clamping and operating arms, into which the other two clip parts are axially inserted in an assembly rotary position and are axially interlocked by subsequent rotation in the direction towards the closed clip position.

8. The surgical clip according to claim 1, wherein the clamping arms are designed in one piece with their clamping arm ends.

9. The surgical clip according to claim 1, wherein the clamping arms are designed in each case in two parts with a clamping arm base and a clamping arm end, and the clamping arm base comprises an interface for fixing the clamping arm end.

10. The surgical clip according to claim 1, wherein the clamping arms are designed in each case as rings that abut each other in the closed clip position and the ring openings of which form a through-hole.

11. The surgical clip according to claim 1, wherein the clamping arms of the two outer clip parts are each designed as a fork and the clamping arm of the middle clip part is designed as a ring.

12. The surgical clip according to claim 1, wherein the clamping arm of one of the two outer clip parts is designed as a fork and the clamping arms of the other two clip parts are each designed as a ring.

* * * * *

UNITED STATES PATENT AND TRADEMARK OFFICE
CERTIFICATE OF CORRECTION

PATENT NO. : 10,226,252 B2
APPLICATION NO. : 14/670709
DATED : March 12, 2019
INVENTOR(S) : Daniel Lazic Page 1 of 1

It is certified that error appears in the above-identified patent and that said Letters Patent is hereby corrected as shown below:

In the Claims

In Column 8, Line 31 (Claim 7), "two outer clip parts" should read --the two outer clip parts--.

In Column 8, Line 47 (Claim 10), "and the ring openings" should read --and ring openings--.

Signed and Sealed this
Fourteenth Day of May, 2019

Andrei Iancu
*Director of the United States Patent and Trademark Office*